United States Patent
Santoso et al.

(10) Patent No.: US 7,981,032 B2
(45) Date of Patent: Jul. 19, 2011

(54) PATIENT MONITORING AND ALARM PROCESSING SYSTEM AND USER INTERFACE

(75) Inventors: Nugroho Iwan Santoso, Plainsboro, NJ (US); Johnnie W. Huang, Peabody, MA (US); Clifford Mark Kelly, Windham, NH (US)

(73) Assignee: Draeger Medical Systems, Inc, Andover, MA (US)

( * ) Notice: Subject to any disclaimer, the term of this patent is extended or adjusted under 35 U.S.C. 154(b) by 780 days.

(21) Appl. No.: 11/165,970

(22) Filed: Jun. 24, 2005

(65) Prior Publication Data

US 2005/0256381 A1 Nov. 17, 2005

Related U.S. Application Data

(62) Division of application No. 10/223,311, filed on Aug. 19, 2002, now Pat. No. 7,224,281.

(60) Provisional application No. 60/316,605, filed on Aug. 31, 2001.

(51) Int. Cl.
*A61B 5/00* (2006.01)

(52) U.S. Cl. .................. 600/300; 128/920; 340/539.12

(58) Field of Classification Search .............. 600/300, 600/301; 340/573.1; 128/903–905, 920
See application file for complete search history.

(56) References Cited

U.S. PATENT DOCUMENTS

| | | | | |
|---|---|---|---|---|
| 4,839,822 A | * | 6/1989 | Dormond et al. | 706/45 |
| 5,724,983 A | * | 3/1998 | Selker et al. | 600/301 |
| 5,819,007 A | * | 10/1998 | Elghazzawi | 706/46 |
| 6,572,542 B1 | * | 6/2003 | Houben et al. | 600/300 |
| 7,022,072 B2 | * | 4/2006 | Fox et al. | 600/365 |

* cited by examiner

*Primary Examiner* — Henry M Johnson, III
*Assistant Examiner* — Kai Rajan
(74) *Attorney, Agent, or Firm* — Jack Schwartz & Associates, PLLC

(57) ABSTRACT

Some embodiments of the invention provide a system to monitor a patient. In some aspects, a signal representing a value of a physiological parameter is received from a monitoring device. The received value is a value that caused the monitoring device to trigger an alarm associated with the psychological parameter. A notification is determined based on the received signal and on a second signal that represents a value of a second physiological parameter. The notification is then presented to an operator.

5 Claims, 5 Drawing Sheets

PATIENT MONITORING AND ALARM PROCESSING SYSTEM AND USER INTERFACE

CROSS-REFERENCE TO RELATED APPLICATIONS

This application claims priority to Provisional Application Ser. No. 60/316,605 filed Aug. 31, 2001 and entitled "A Smart Alarm and Decision Support System and is a Divisional Application of Non-Provisional application Ser. No. 10/223,311 filed Aug. 19, 2002, now U.S. Pat. No. 7,224,281.

TECHNICAL FIELD

The present invention relates to medical systems and in particular to systems for monitoring patient physiological parameters.

BACKGROUND

Patient treatment often includes monitoring of various physiological parameters. Conventionally, such monitoring begins by attaching sensors to several locations on a patient's body. The sensors transmit signals to one or more devices, which in turn determine the values of subject parameters based on the signals. In this regard, a particular parameter value may be determined based on a signal received from one or more of the attached sensors.

Most conventional monitoring devices include alarm functions. Generally, a device issues an audible and/or visual alarm after determining that a particular parameter value has fallen outside a specified range. This arrangement presents numerous difficulties. First, a monitoring device may issue an alarm in a case that an associated sensor detaches from the patient or in case of other non-emergency situations. Several monitoring devices are often used to monitor a single patient, with each device presenting a possibility of a false alarm. These possibilities condition caregivers to reduce their sensitivity to the alarms.

A caregiver's decision-making processes are often prolonged during critical events due to a barrage of corresponding alarms from multiple monitoring devices, some of which may be false alarms. Additionally, an alarm usually fails to provide sufficient information to a caregiver. Most patient complications are evidenced by several physiological parameters, so an alarm-triggering value of one parameter is insufficient to identify a particular complication.

In view of the foregoing, a more efficient system to process patient alarms is desired.

SUMMARY

Some embodiments of the invention provide a system to monitor a patient. In some aspects, a signal representing a value of a physiological parameter is received from a monitoring device. The received value is a value that caused the monitoring device to trigger an alarm associated with the psychological parameter. A notification is determined based on the received signal and on a second signal that represents a value of a second physiological parameter. The notification is then presented to an operator.

According to some aspects, probabilities associated with the notification are presented to the operator. The probabilities indicate a calculated likelihood that the notification describes the patient's condition. Some aspects also allow the operator to issue an instruction to suppress a particular notification, in response to which a notification is determined based on an assumption that the particular notification is not indicative of the patient's condition.

The present invention should not be deemed limited to the disclosed embodiments, however, as those of ordinary skill in the art can readily adapt the teachings of the present invention to create other embodiments and applications.

BRIEF DESCRIPTION OF THE DRAWINGS

The exact nature of this invention, as well as its advantages, will become readily apparent from consideration of the following specification as illustrated in the accompanying drawings, wherein.

DETAILED DESCRIPTION

The following description is provided to enable any person of ordinary skill in the art to make and use the invention and sets forth the best modes contemplated by the inventor for carrying out the invention. Various modifications, however, will remain readily apparent to those in the art.

Figure 1:
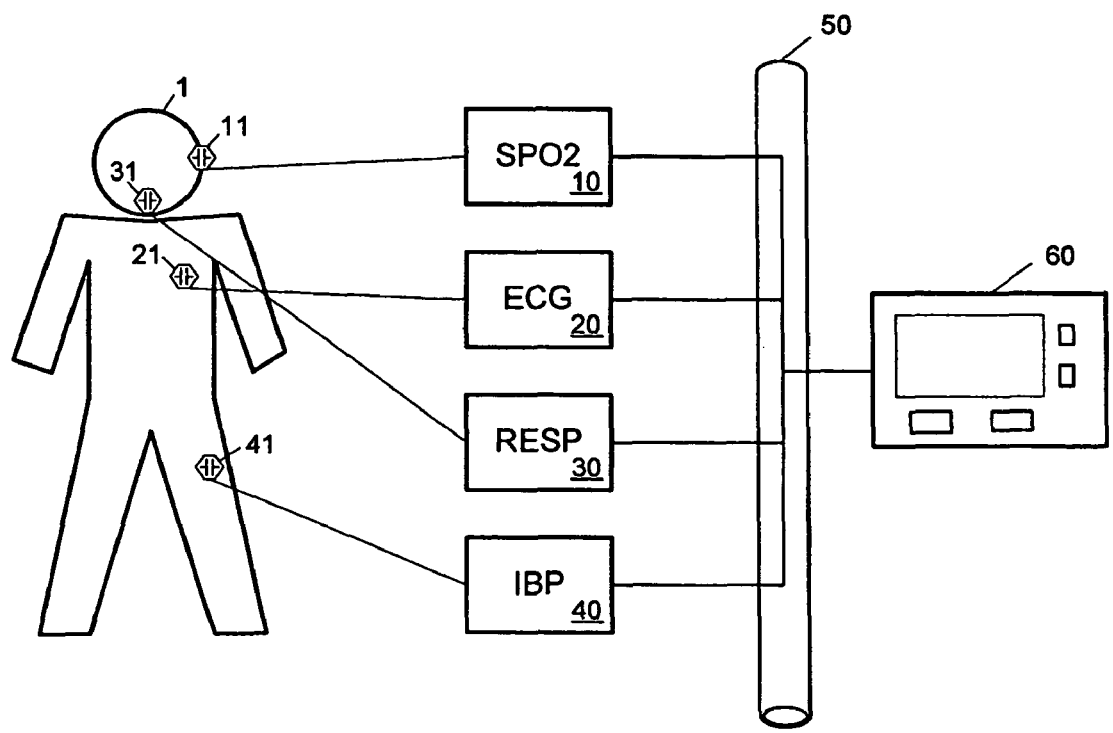
FIG. 1 is diagram illustrating patient monitoring according to some embodiments of the present invention.

FIG. 1 illustrates a patient monitoring system according to some embodiments of the present invention. The system illustrated in FIG. 1 may be used in any number of locations and in any number of situations. Possible locations include a hospital, an office, and an ambulance, and possible situations include during an operation, during a checkup, and during a recovery period.

Attached to patient 1 are monitoring devices such as sensors for producing signals associated with physiological parameters. The produced signals are received by monitoring devices such as monitors for determining a value of a physiological parameter therefrom. More specifically, blood oxygen saturation level (SPO2) monitor 10 receives a signal associated with an SPO2 parameter from sensor 11, electrocardiogram (ECG) monitor 20 receives a signal associated with a heart rate (HR) parameter from sensor 21, respiration (RESP) monitor 30 receives a signal associated with a RESP parameter from sensor 31, and invasive blood pressure (IBP) monitor 40 receives a signal associated with an IBP parameter from sensor 41. Each of sensors 11, 21, 31 and 41 is a sensor suitable to produce a signal representing an associated parameter. Accordingly, each monitor is used to determine a value of an associated parameter. In some embodiments, the signal received from SPO2 monitor 10 may also be used to determine a value of a pulse (PLS) parameter.

It should be noted that, according to some embodiments, one or more of monitors 10 through 40 may receive signals from more than one sensor and/or two or more of monitors 10 through 40 may receive signals from a same sensor. In addition, each sensor may transmit a signal using any currently or hereafter-known system for transmitting data, including RF, infrared, or fiber-optic. Moreover, the signals may be transmitted over one or more of an IP network, an Ethernet network, a Bluetooth network, a cellular network, and any other suitable network.

Monitors 10 through 40 are in communication with communication bus 50. Again, communication bus 50 may comprise any type of network, and communication therewith may proceed in accordance with any hardware and/or software protocol. It should be noted that the elements described herein as being in communication with one another need not be continuously exchanging data. Rather, in some embodiments, a connection is established prior to each exchange of data and is severed thereafter.

Also in communication with communication bus 50 is alarm server 60. According to some embodiments, alarm server 60 operates to receive a signal representing a value of a physiological parameter, wherein the value has triggered an alarm associated with the psychological parameter, to determine a notification based at least on the received signal and on a second signal representing a value of a second physiological parameter, and to present the notification to an operator.

In some embodiments, alarm server 60 includes a communication interface for receiving physiological parameter values from monitors 10 through 40, a prediction unit for providing data representing an extrapolated patient condition based on the values, a decision processor for applying a decision rule to the extrapolated patient condition to identify an alert condition, and an alert generator for generating an alert indication in response to the alert condition. The prediction unit may use patient record information for extrapolating the patient condition. In some embodiments, the generator provides treatment and/or diagnostic suggestions based on the extrapolated condition. The generator may also provide user-selectable suggestion information of different degrees of detail with respect to the extrapolated condition, and may also associate different reliability weighting with corresponding suggestion information of different degrees of detail.

More specifically, according to some embodiments, alarm server 60 receives signals from monitors 10 through 40. Each of the signals represents a value of a respective physiological parameter. At least one of the values has triggered an alarm of its respective monitor because the value falls outside of a range of predetermined values. For example, SPO2 monitor 10 has been programmed to issue an alarm if it determines an SPO2 value that is less than 80%. SPO2 monitor 10 receives a signal from sensor 11, determines an SPO2 value of 70% based on the signal, and issues an alarm because the determined value is less than 80%. SPO2 monitor 10 transmits a signal representing the value to alarm server 60 via communication bus 50. One or more of monitors 20 through 40 also sends a signal representing a value of a physiological parameter to alarm server 60. The signals received from the one or more monitors may or may not have triggered an alarm of their respective monitors. In this regard, SPO2 monitor 10 may also transmit signals representing parameter values that do not trigger an alarm to alarm server 60.

Alarm server 60 determines one or more notifications based on the received signals and presents the one or more notifications to an operator. The notifications indicate a condition of patient 1 based on the received signals. According to some embodiments, alarm server 60 also determines a probability corresponding to each notification and presents the probabilities in association with their corresponding notifications. Systems for determining the notifications and probabilities will be described in detail below.

In some embodiments, the operator can issue a command to suppress one of the presented notifications. In such a case, future reception of similar signals would result in alarm server 60 determining subsequent notifications that do not include the suppressed notification. The subsequent notifications are determined in some embodiments based on an assumption that the suppressed notification is not indicative of the patient's condition. Suppression of certain notifications that are known not to describe a patient's condition may result in the determination of more reliable notifications and more accurate associated probabilities. Notification suppression according to some embodiments of the present invention is described below.

Figure 2:
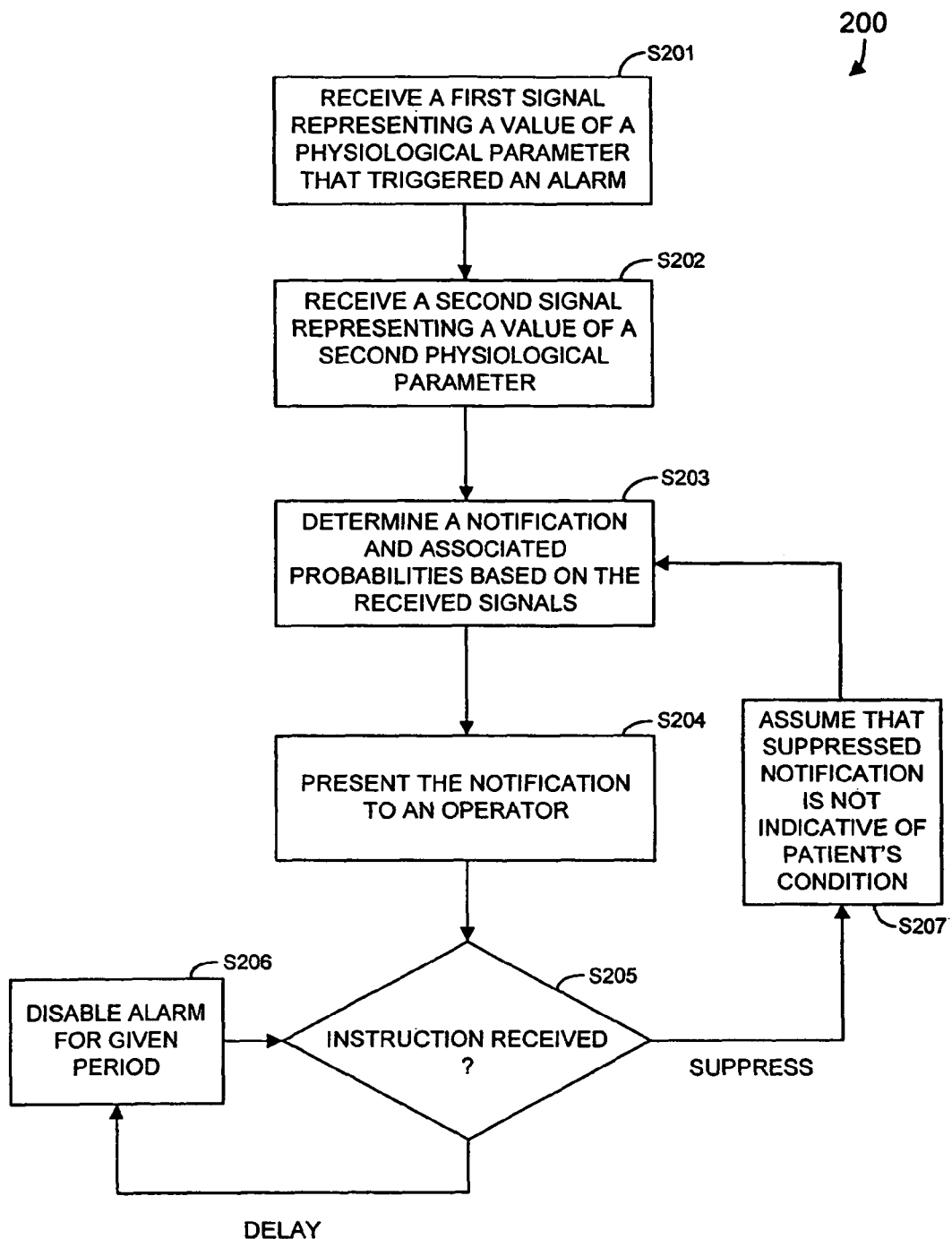
FIG. 2 is a flow diagram illustrating process steps according to some embodiments of the present invention.

FIG. 2 is a flow diagram of process steps 200 according to some embodiments of the present invention. Although process steps 200 are described as being performed by alarm server 60, hardware and/or software for executing process steps 200 may be located in and/or executed by one or more of sensors 11 through 41, monitors 10 through 40, and alarm server 60.

Initially, at step S201, alarm server 60 receives a first signal that represents a value of a physiological parameter. The represented value triggered an alarm prior to step S201 because a device recognized the value as satisfying an alarm condition. The device may be a device that determined the value, a device that issued the alarm, and/or another device. According to the present example, a signal is received in step S201 from SPO2 monitor 10 that represents an SPO2 value of 70%. This value has triggered an alarm of SPO2 monitor 10 because the value is less than 80%.

Next, in step S202, alarm server 60 receives a second signal that represents a value of a second parameter. The value of the second parameter may or may not have triggered an alarm prior to step S202. A signal representing a HR value of 110 is received from ECG monitor 20 in the present example of step S202. Notifications and associated probabilities are determined in step S203 based on the first and second signals. It should be noted that the determination may be based on additional signals representing values of additional physiological parameters. For example, the determination of the present example may also be based on a signal received from monitor 10 that represents a PLS value of 104.

The determined notifications are intended to describe the condition of patient 1, and the associated probabilities are intended to express a likelihood that the notification is accurate. Many systems can be used to determine the notifications and the associated probabilities. These systems may be based on one or more of rules, expert systems, probabilistic networks, predictive networks, neural networks, and the like. According to a specific example, an expert-Bayesian network may be used in step S203.

One known method of creating an expert-Bayesian network begins with the creation of an expert knowledge diagram. Generally, the diagram illustrates the approach an expert would take in making a determination based on various inputs. In the present instance, an expert knowledge map associates physiological values with possible causes of the values via probability distributions. Once an expert knowledge map is created, the probability distributions may be used to derive a corresponding expert-Bayesian network. Known adaptive normalization techniques may be applied to "train" the expert-Bayesian network based on its intended use.

Figure 3A:
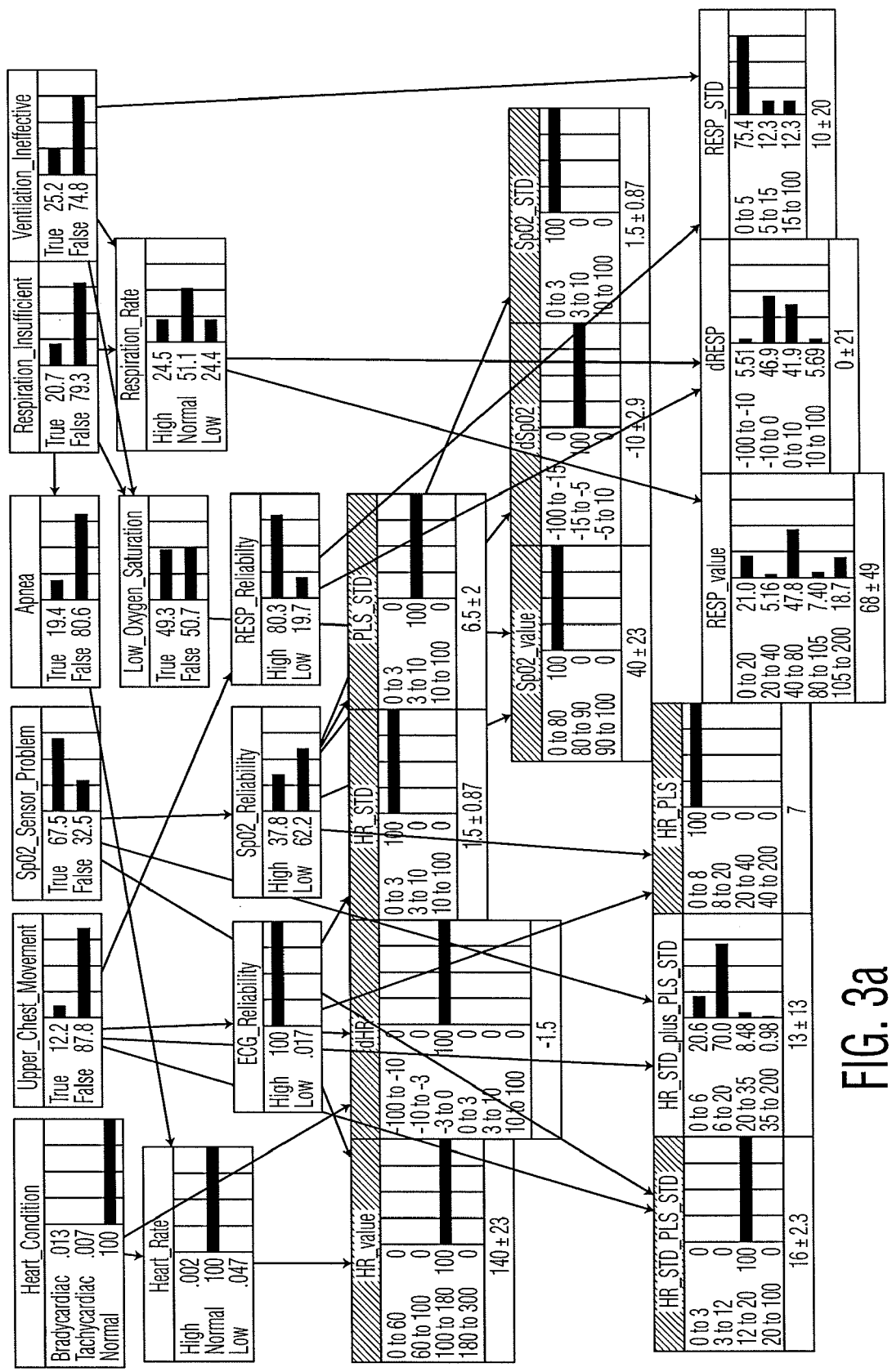
FIGS. 3a and 3b comprise expert-Bayesian networks for use in conjunction with some embodiments of the present invention.

FIG. 3a illustrates an expert-Bayesian network for use in conjunction with some embodiments of step S203. The nodes of the two upper-most levels of the network determine probabilities associated with notifications. The third level includes three nodes representing intermediate determinations that are made based on determined physiological parameters. Each node of the network includes a mathematical function that determines a probability of particular scenarios based on the outputs of nodes from which the node receives input. In a specific example, the "dHR" node of FIG. 3a may include the following mathematical function, which, as shown in FIG. 3a, operates on the outputs of the "Heart_Condition" and "ECG_Reliability" nodes:

```
p (dHR|ECG_Reliability, Heart_Condition) = (ECG_Reliability ==
High && Heart_Condition == Bradycardiac) ? NormalDist(dHR, -5, 2):
(ECG_Reliability == High && Heart_Condition == Tachycardiac) ?
NormalDist(dHR, 5, 2): (ECG_Reliability == High &&
Heart_Condition == Normal) ? NormalDist(dHR, 0, 1):
(ECG_Reliability == Low && Heart_Condition == Bradycardiac) ?
NormalDist(dHR, -5, 15): (ECG_Reliability == Low &&
Heart_Condition == Tachycardiac) ? NormalDist(dHR, 5, 15):
(ECG_Reliability == Low && Heart_Condition == Normal) ?
NormalDist(dHR, 0, 20): 0
```

This function determines a probability table as shown below:

| ECG_Reliability | Heart_Condition | | |
|---|---|---|---|
| | Bradycardiac | Tachycardiac | Normal |
| High | n(dHR, -5, 2) | n(dHR, 5, 2) | n(dHR, 0, 1) |
| Low | n(dHR, -5, 15) | n(dHR, 5, 15) | n(dHR, 0, 20) |

Accordingly, the data shown in cell (1, 1) indicates that in a state where ECG_Reliability = High and Heart_Condition = Bradycardiac, dHR may be expressed by a normal distribution having mean = -5 and standard deviation = 2.

It should be noted that the inputs to a node may themselves consist of probability distributions. For example, one node of the third level represents a probability that a received RESP value has a High reliability and a probability that the received RESP value has a Low reliability based on a probability distribution of the derivative of the RESP value and a probability distribution of the standard deviation of the RESP value.

The grayed-out nodes of FIG. 3a are not associated with probability distributions because the actual values represented by the nodes are known. According to the present example, the grayed-out nodes represent values received by alarm server 60 in steps S201 and S202. Therefore, the probabilities reflected within the other nodes of FIG. 3a are based on the received values and on the mathematical functions included in the nodes. More particularly, based on the received values of 70% SPO2, 110 HR and 104 PLS, the notifications and probabilities of the two upper-most levels of the FIG. 3a network are determined in step S203. It should be noted that only one notification and/or no probability is determined in some embodiments of step S203.

Figure 4A:
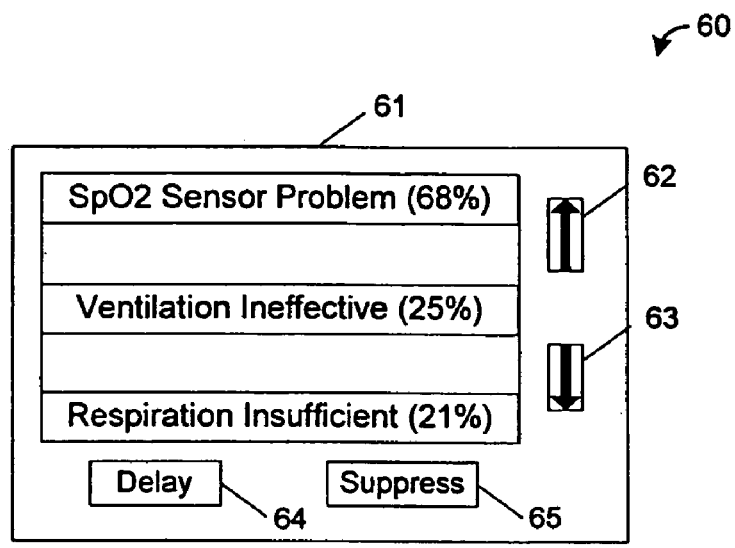
FIGS. 4a and 4b are outward views of displays presenting notifications and associated probabilities according to some embodiments of the present invention.

The notifications and the associated probabilities are presented to an operator in step S204. FIG. 4a is an outward view of interface 61 of alarm server 60 for use in presenting the notifications and the associated probabilities. Interface 61 of FIG. 4a presents notifications and associated probabilities determined based on the network of FIG. 3a. As shown, all notifications and/or associated probabilities determined in step S203 need not be presented in step S204. For example, presented in step S204 might be only those notifications associated with probabilities of greater than 20% and/or those notifications describing a critical condition and that are associated with a probability of greater than 50%.

Interface 61 also includes buttons 62 and 63 for selecting one of the displayed notifications, button 64 for delaying an alarm, and button 65 for suppressing a selected notification. According to some embodiments, the alarm that was triggered by the value of the signal received in step S201 continues throughout steps S201 through S205. An operator may issue an instruction to temporarily disable the alarm by pressing button 64. In this case, the instruction is detected in step S205 and flow proceeds to step S206, in which the alarm is temporarily disabled for a specified period. Any other alarms issued by monitoring devices 20 through 40 may also be disabled in step S206. The disabled alarms resume after expiration of the specified period.

The operator may issue an instruction to ignore a presented notification by selecting the notification using buttons 62 and/or 63 and by thereafter pressing button 65. In some instances, the operator may issue such an instruction because the operator is confident that the selected notification does not describe the condition of patient 1. According to the present example, the operator selects the "SPO2 Sensor Problem" notification and presses button 65. The instruction is received in step S205, and flow thereafter proceeds to step S207.

Figure 3B:
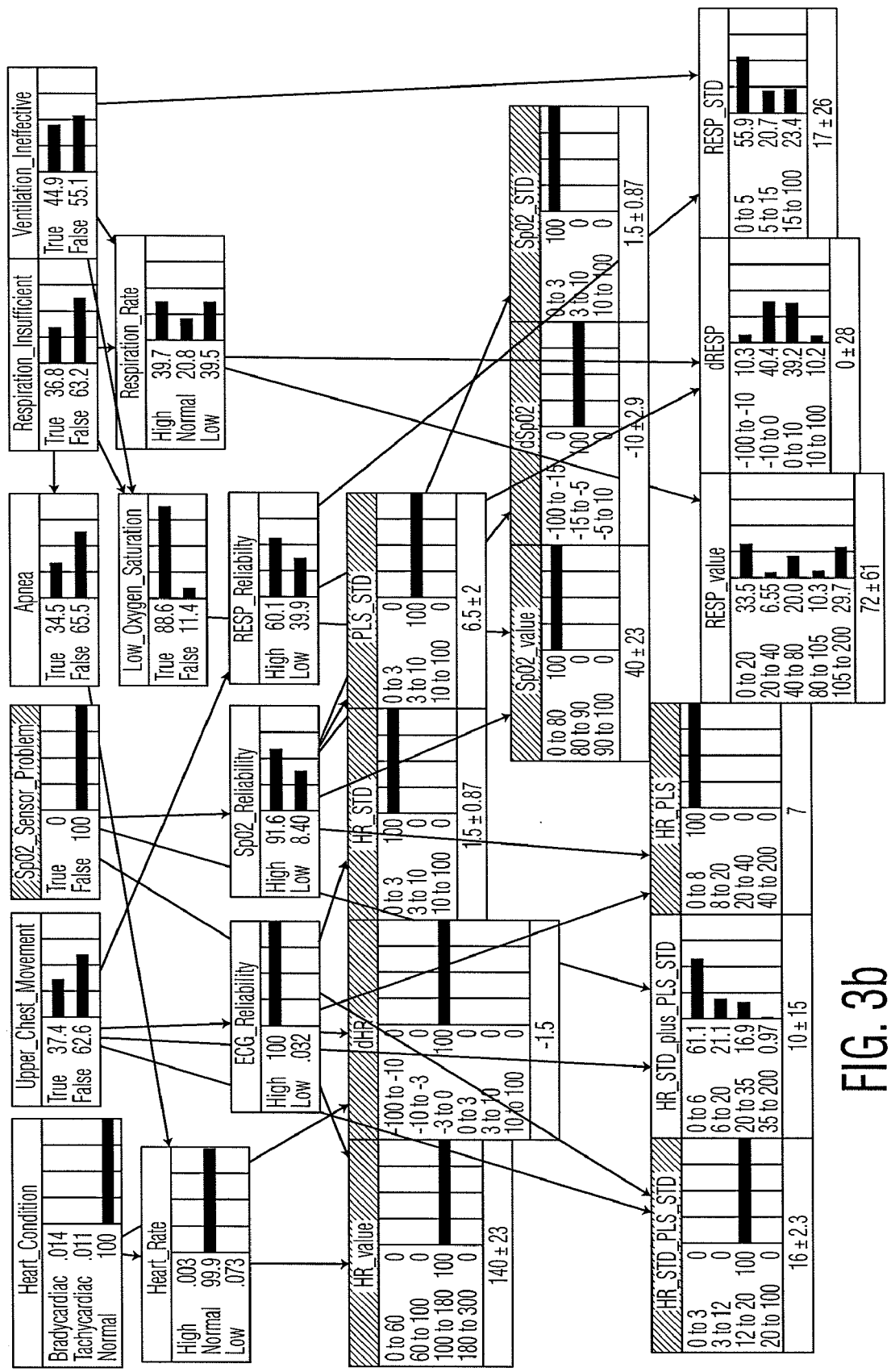

In step S207, it is assumed that the selected notification is not indicative of the patient's condition. Flow returns to step S203 to re-determine the notifications and associated probabilities based on this assumption. FIG. 3b illustrates this re-determination using the expert-Bayesian network of FIG. 3a. More particularly, the probability associated with the "SPO2 Sensor Problem" notifications has been forced to 0% and each other node has been recalculated based thereon and on the original values of the SPO2, HR and PLS parameters.

Figure 4B:
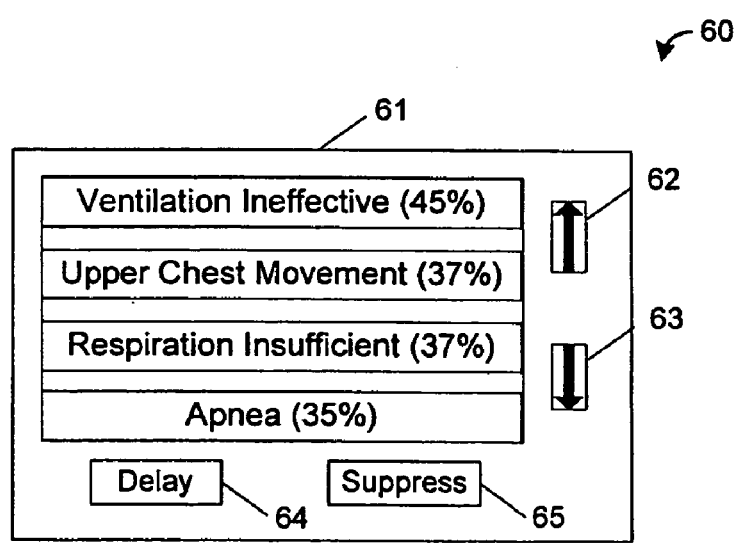

The re-determined notifications and associated probabilities are presented to the operator in step S204. FIG. 4b is a view of interface 61 presenting the re-determined notifications and probabilities according to some embodiments of the present invention. As shown, the "SPO2 Sensor Problem" notification has been suppressed.

Those in the art will appreciate that various adaptations and modifications of the above-described embodiments can be configured without departing from the scope and spirit of the invention. In some embodiments, functions attributed above to monitors 10 through 40 are performed by a single monitoring unit, such as the Siemens Infinity Patient Monitoring System™. Some embodiments also incorporate the functions of alarm server 60 into the single monitoring unit.

Embodiments of the present invention may differ from the description of process steps 200. For example, in some embodiments, no probability is determined in step S203 or presented in step S204. According to some embodiments, alarm server 60 may receive a signal from a monitoring device representing a value of a physiological parameter that is not associated with any node of a probabilistic network used by alarm server 60 but that triggered an alarm of the monitoring device. As a result, alarm server 60 presents a notification of the alarm on interface 61 along with other notifications that are determined as described above. Such an arrangement allows alarm server 60 to handle alarms other than those alarms that it has been programmed to analyze in conjunction with other signals.

In some embodiments, the operator may also issue an instruction to discontinue suppression of a notification. The particular arrangement of process steps 200 is not meant to imply a fixed order to the steps; embodiments of the present invention can be practiced in any order that is practicable. In this regard, flow may proceed from step S207 to step S201 to determine notifications and/or probabilities based on a command to suppress a notification and on newly-received parameter values.

Therefore, it is to be understood that, within the scope of the appended claims, the invention may be practiced other than as specifically described herein.

What is claimed is:

1. A medical alarm system for processing information from a plurality of patient monitoring devices adapted to be attached to a patient and having at least one physiological sensor that produces a signal representing at least one patient physiological parameter and transmit the signal via a communications network, the system comprising:
a communication interface configured to receive a signal representing patient physiological parameter values from the plurality of patient monitoring devices for a particular patient via the communications network;
a processor configured to
analyze said received signal representing patient physiological parameter values, provide data representing a plurality of notifications to an operator, each notification corresponding to an extrapolated patient condition, and trigger said alert indication when a respective notification indicates a predetermined patient physiological parameter value has been reached,
receive a command from an operator to suppress one of said triggered notifications that is not indicative of the patient's medical condition, and
recalculate said data representing said plurality of notifications to exclude said suppressed notification;
a decision processor that applies a decision rule to said extrapolated patient condition derived from said recalculated notifications to identify an alert condition is present; and
an alert generator that generates said alert indication in response to said identified alert condition.

2. A system according to claim 1, wherein
said device uses patient record information for a particular patient in extrapolating patient condition.

3. A medical alarm system for processing information from a plurality of patient monitoring devices adapted to be attached to a patient and having at least one physiological sensor that produces a signal representing at least one patient physiological parameter and transmit the signal via a communications network, the system comprising:
a communication interface configured to receive a signal representing patient physiological parameters from the plurality of patient monitoring devices for a particular patient via the communications network;
a processor configured to
analyze said received signal representing patient physiological parameter values, provide data representing a plurality of notifications to an operator, each notification corresponding to an extrapolated patient condition, and trigger said alert indication when a respective notification indicates a predetermined patient physiological parameter value has been reached,
receive a command from an operator to suppress one of said triggered notifications that is not indicative of the patient's medical condition, and
recalculate said data representing said
plurality of notifications to exclude said suppressed notification; and
a generator that provides at least one of, (a) diagnostic and (b) treatment suggestions based on said extrapolated patient condition derived from said recalculated notifications.

4. A system according to claim 3, wherein:
said generator provides user-selectable suggestion information concerning said notification.

5. A system according to claim 4, wherein
said generator associates different reliability weighting to corresponding suggestion information.

* * * * *